United States Patent [19]

Maerkl et al.

[11] Patent Number: 4,925,972
[45] Date of Patent: May 15, 1990

[54] PREPARATION OF ALKYL PENTENOATES

[75] Inventors: Robert Maerkl, Fussgoenheim; Wolfgang Harder, Weinheim, both of Fed. Rep. of Germany

[73] Assignee: BASF Aktiengesellschaft, Ludwigshafen, Fed. Rep. of Germany

[21] Appl. No.: 378,794

[22] Filed: Jul. 12, 1989

[30] Foreign Application Priority Data

Jul. 26, 1988 [DE] Fed. Rep. of Germany ....... 3825296

[51] Int. Cl.$^5$ ............................................. C07C 67/38
[52] U.S. Cl. .................................... 560/206; 560/204; 562/598
[58] Field of Search ................. 560/206, 204; 562/598

[56] References Cited

U.S. PATENT DOCUMENTS

| | | | |
|---|---|---|---|
| 3,778,466 | 12/1973 | Matsuda | 560/206 |
| 4,256,909 | 3/1981 | Kummer et al. | 560/204 |
| 4,360,692 | 11/1982 | Kummer et al. | 560/175 |
| 4,421,691 | 12/1983 | Müller et al. | 260/410.9 R |
| 4,550,195 | 10/1985 | Platz et al. | 560/206 |

FOREIGN PATENT DOCUMENTS 0010581 2/1981 European Pat. Off. .

Primary Examiner—Werren B. Lone
Assistant Examiner—Vera C. Clarke
Attorney, Agent, or Firm—Keil & Weinkauf

[57] ABSTRACT

Alkyl pentenoates are prepared by
(a) reacting butadiene or a butadiene-containing hydrocarbon mixture with carbon monoxide and an alkanol in the presence of a tertiary aromatic heterocyclic nitrogen base and a cobalt carbonyl catalyst at from 80° to 160° C. under from 100 to 1,000 bar to obtain a reaction mixture which contains alkyl pentenoate, $C_6$-diester, tertiary nitrogen base, alkanol, butadiene, hydrocarbon and by-product,
(b) substantially removing from the reaction mixture obtained any excess hydrocarbon, nitrogen base, alkanol and alkyl pentenoate by distillation to obtain a residue which contains cobalt carbonyl catalyst,
(c) bringing the residue which contains cobalt carbonyl catalyst into contact with a mixture of carbon monoxide and hydrogen at elevated temperature and elevated pressure, and
(d) recycling the residue which contains cobalt carbonyl catalyst into alkyl pentenoate synthesis stage (a).

6 Claims, No Drawings

PREPARATION OF ALKYL PENTENOATES

U.S. Pat. No. 4,550,195 discloses for preparing alkyl pentenoates by reacting butadiene-containing $C_4$ cuts with carbon monoxide and alkanols in the presence of cobalt carbonyl catalysts and heterocyclic aromatic tertiary nitrogen bases. In the industrial practice of the process it was found to be desirable to reuse the catalyst. However, the resulting space-time yield was found to leave something to be desired.

Similarly, in the process for preparing pentenoic esters by carbalkoxylation of butadiene described in Bull. Chem. Soc. Jap. 46 (1973), 125, the reuse of the cobalt catalyst constantly diminishes the conversion of butadiene and increases the proportion of by-products.

In the process described in European Patent No. 10 581, the reaction mixture obtained in the course of alkyl pentenoate preparation is cooled down and separated into two phases, and the phase which contains the cobalt catalyst is partially recycled. However, it has been found that phase separation presents problems. In addition, the phase which contains the cobalt catalyst also contains up to 30% of pentenoic ester, which in turn is recycled and becomes available for further reactions.

It is an object of the present invention, in the preparation of alkyl pentenoate by carbalkoxylation of butadiene with catalyst recycling, to increase the space-time yield of alkyl pentenoate while maintaining a high selectivity and a high conversion and without increasing the formation of by-products.

We have found that this object is achieved by a process for preparing an alkyl pentenoate by (a) reacting butadiene or a butadiene-containing hydrocarbon mixture with carbon monoxide and an alkanol in the presence of a tertiary aromatic heterocyclic nitrogen base and a cobalt carbonyl catalyst at from 80° to 160° C. under from 100 to 1,000 bar to obtain a reaction mixture which contains alkyl pentenoate, $C_6$-diester, tertiary nitrogen base, alkanol, butadiene, hydrocarbon and by-product, (b) substantially removing from the reaction mixture obtained any excess hydrocarbon, nitrogen base, alkanol and alkyl pentenoate by distillation to obtain a residue which contains cobalt carbonyl catalyst, (c) bringing the residue which contains cobalt carbonyl catalyst into contact with a mixture of carbon monoxide and hydrogen at elevated temperature and elevated pressure, and (d) recycling the residue which contains cobalt carbonyl catalyst into alkyl pentenoate synthesis stage (a).

The novel process has the advantage that the space-time yield is not just undiminished but actually increased. Furthermore, the novel process has the advantage that a high conversion of butadiene is obtained coupled with the high selectivity to alkyl pentenoate. Moreover, the novel process has the advantage that the formation of by-products is not increased.

The starting compound in stage (a) is butadiene or a butadiene-containing hydrocarbon mixture. It is advantageous to use butadiene-containing $C_4$ cuts. Such $C_4$ cuts contain for example on average from 40 to 60% by weight of butadiene, from 20 to 35% by weight of isobutene, from 10 to 15% by weight of butene-1, from 2 to 15% by weight of butene-2 and from 1 to 10% by weight of butane.

Suitable alkanols advantageously have from 1 to 6 carbon atoms, in particular from 1 to 4 carbon atoms. Specific examples are: methanol, ethanol, isopropanol, butanol and hexanol. Particular preference is given to methanol.

The alkanol is in general used in excess. An advantageous amount is from 1.1 to 10 moles, in particular from 1.5 to 5 moles, of alkanol per mole of butadiene.

The reaction is carried out at from 80° to 160° C., in particular at from 100° to 150° C. Furthermore, the reaction is maintained under from 100 to 1,000 bar, in particular from 120 to 700 bar.

Carbon monoxide is advantageously used in excess, for example in from 1.3 to 10 times the stoichiometrically required amount. If the process is carried out continuously, excess carbon monoxide is constantly recycled and replenished with fresh carbon monoxide.

The cobalt carbonyl catalyst used is either generated in situ from a cobalt salt, for example from a cobalt salt of a fatty acid, such as cobalt formate, acetate, propionate or butyrate, or advantageously introduced as ready-prepared cobalt carbonyl. It is particularly useful to introduce the cobalt carbonyl catalyst into the reaction mixture in a solution in butadiene or a $C_4$ cut. Such a solution is obtained for example by reacting an aqueous solution of a fatty acid cobalt salt with a mixture of carbon monoxide and hydrogen in the presence of activated carbon at from 100° to 175° C. under from 100 to 400 bar. The cobalt carbonyl compound formed is then extracted from the aqueous solution with butadiene or a butadiene-containing hydrocarbon mixture.

The reaction is carried out in the presence of a heterocyclic aromatic tertiary nitrogen base which advantageously has a $pK_A$ value of from 6 to 9. Suitable nitrogen bases are for example 3-methylpyridine ($pK_A$ 7.0), 4-methylpyridine, 3,5-dimethylpyridine, quinoline and isoquinoline. It is also possible to use mixtures of the nitrogen bases mentioned. Particular preference is given to using 3-methylpyridine or 4-methylpyridine or mixtures thereof. It is particularly advantageous to use from 2 to 25 moles of the abovementioned nitrogen bases per mole of cobalt carbonyl catalyst.

The amount of cobalt carbonyl catalyst used per mole of butadiene is advantageously from 0.01 to 0.25 mole, in particular from 0.04 to 0.2 mole.

The reaction mixture obtained contains alkyl pentenoate, small amounts of $C_6$-diester, tertiary nitrogen base, excess alkanol, unconverted butadiene, any further hydrocarbon from the starting material, and unidentifiable by-products, such as polymeric butadiene. The reaction mixture is advantageously depressurized and distilled to remove methyl pentenoate, nitrogen base, excess alkanol and hydrocarbon (stage b). The distillation is advantageously carried out at a base of column temperature of from 50° to 55° C. under a pressure of from 10 to 20 mbar. The bottom product obtained is a residue which contains cobalt catalyst together with nitrogen base and residues of pentenoic ester, $C_6$-diester and high-boilers. A typical mixture contains for example from 9 to 12% by weight of cobalt as cobalt carbonyl complex, from 25 to 35% by weight of nitrogen base, from 3 to 10% by weight of pentenoic ester, from 2 to 6% by weight of $C_6$-diester and from 45 to 55% by weight of high-boiling residue.

In a subsequent stage (c) the residue which contains the cobalt catalyst is brought into contact with a mixture of carbon monoxide and hydrogen at elevated temperature and pressure. Advantageously, this means a temperature of from 50° to 200° C., in particular from 100° to 180° C., and for example a pressure of from 10 to 300 bar, in particular from 50 to 200 bar.

It is advantageous to use a mixture of from 10 to 90% by volume of carbon monoxide and from 10 to 90% by volume of hydrogen. It is further advantageous to carry out the treatment for a period of from 5 to 200, in particular from 10 to 150, minutes. The mixture of carbon monoxide and hydrogen is then separated off.

The catalyst residue thus treated is recycled into the pentenoic ester synthesis stage (a).

In a preferred procedure, a portion, for example from 20 to 90% by weight, of the residue thus treated is recycled into the pentenoic ester synthesis, and the catalyst present is replenished by a fresh catalyst, while the remainder, i.e. from 10 to 80% by weight, is used as a catalyst for the carbalkoxylation of pentenoic esters to adipic esters. In said process, after the useful products have been separated off, the remaining catalyst is worked up, which thus also removes high boilers. This has the advantage that the high boilers do not continuously build up in the catalyst system. A suitable method is described for example in EP No. 10 581.

The process of the invention is illustrated by the Examples below. The parts by weight bear the same relationship to the parts by volume as the kg to the liter.

EXAMPLE 1

A high-pressure vessel of 4 by parts volume capacity is charged from below in the course of 60 minutes with 9.4 parts by weight of recycled catalyst from the carbalkoxylation of butadiene to methyl pentenoate, obtained by removal of the volatile components, 10% (m/m) of cobalt as cobalt carbonyl complex, 31% (m/m) of 3-methylpyridine, 6% (m/m) of methyl pentenoate, 4% (m/m) of $C_6$-diester, 48% (m/m) of residue and 0.66 part by weight of a gas mixture of 51% (v/v) of carbon monoxide and 49% (v/v) of hydrogen. The activation of the cobalt carbonyl catalyst was carried out at 160° C. under 100 bar. After this mixture had been depressurized to 1 bar, 26.4 parts by weight of a $C_4$ cut containing 41% (m/m) of 1,3-butadiene, 19.5 parts by weight of 3-methylpyridine, 8.8 parts by weight of methanol and 21.6 parts by weight of a gas mixture of the following composition: 83% by volume of carbon monoxide, 1% by volume of carbon dioxide, 3% by volume of nitrogen, 0.07% by volume of hydrogen and 12% by volume of butenes, were added. The carbalkoxylation takes place at 135° C. under 650 bar in a high-pressure vessel of 260 parts by volume capacity. The product withdrawn at the top of the high-pressure vessel is depressurized, and the gas phase is separated off. The excess $C_4$-hydrocarbons are then distilled off. They still contain 1200 ppm of unconverted butadiene. The conversion, based on butadiene, is 99.8%, and the selectivity for methyl pentenoate is 90%. The space-time yield is 0.079 kg of methyl pentenoate per liter of reaction space per hour.

COMPARATIVE EXAMPLE

Example 1 is repeated, except that the activation of the cobalt carbonyl catalyst is carried out at room temperature and only 7.2 parts by weight of this catalyst mixture are reacted with 0.51 part by weight of the carbon monoxide/hydrogen mixture. This solution is depressurized to 1 bar and has added to it 20.2 parts of a $C_4$ cut containing 41% of 1,3-butadiene, 14.9 parts by weight of 3-methylpyridine, 6.7 parts by weight of methanol and 17.0 parts by weight of the abovementioned gas mixture. The carbonylation is carried out as described in Example 1. The conversion, based on butadiene, is 99.8%, and the selectivity for methyl pentenoate is again 90%. The space-time yield is 0.060 kg of methyl pentenoate per liter of reaction space per hour.

We claim:
1. A process for preparing an alkyl pentenoate by
   (a) reacting butadiene or a butadiene-containing hydrocarbon mixture with carbon monoxide and an alkanol in the presence of a tertiary aromatic heterocyclic nitrogen base and a cobalt carbonyl catalyst at from 80° to 160° C. under from 100 to 1,000 bar to obtain a reaction mixture which contains alkyl pentenoate, $C_6$-diester, tertiary nitrogen base, alkanol, butadiene, hydrocarbon and by-product,
   (b) substantially removing from the reaction mixture obtained any excess hydrocarbon, nitrogen base, alkanol and alkyl pentenoate by distillation to obtain a residue which contains cobalt carbonyl catalyst,
   (c) bringing the residue which contains cobalt carbonyl catalyst into contact with a mixture of carbon monoxide and hydrogen at elevated temperature and elevated pressure, and
   (d) recycling the residue which contains cobalt carbonyl catalyst into alkyl pentenoate synthesis stage (a).

2. A process as claimed in claim 1, wherein a pressure of from 10 to 300 bar is maintained in stage (c).

3. A process as claimed in claim 1, wherein a temperature of from 50° to 200° C. is maintained in stage (c).

4. A process as claimed in claim 1, wherein a mixture of from 10 to 90% by volume of carbon monoxide and from 10 to 90% by volume of hydrogen is used in stage (c).

5. A process as claimed in claim 1, wherein a treatment time of from 10 to 150 mintues is maintained in stage (c).

6. A process as claimed in claim 1, wherein from 20 to 90% by weight of the cobalt carbonyl catalyst is contacted with a mixture of carbon monoxide and hydrogen and recycled into the pentenoic ester synthesis.

* * * * *